United States Patent [19]

Burtscher et al.

[11] Patent Number: 5,523,224
[45] Date of Patent: Jun. 4, 1996

[54] RECOMBINANT D-HYDANTOINASE, A PROCESS FOR THE PRODUCTION AND USE

[75] Inventors: Helmut Burtscher, Habach; Gunter Lang, Tutzing; Friedrich Popp, Sindelsdorf, all of Germany

[73] Assignee: Boehringer Mannheim GmbH, Mannheim, Germany

[21] Appl. No.: 289,709

[22] Filed: Aug. 12, 1994

[30] Foreign Application Priority Data

Aug. 27, 1993 [DE] Germany ............... 43 28 829.4

[51] Int. Cl.⁶ .................................................. C12N 9/86
[52] U.S. Cl. .................................................. 435/231
[58] Field of Search ............................. 435/69.1, 172.3, 435/195, 252.33, 231, 106

[56] References Cited

U.S. PATENT DOCUMENTS 4,912,044  3/1990  Jacob et al. ............... 435/172.3

Primary Examiner—Robert A. Wax
Assistant Examiner—Lisa J. Hobbs
Attorney, Agent, or Firm—Felfe & Lynch

[57] ABSTRACT

A recombinant protein with D-hydantoinase activity which has the amino acid sequence SEQ ID NO 1 is obtainable in large amounts and has an improved temperature stability.

1 Claim, 1 Drawing Sheet

RECOMBINANT D-HYDANTOINASE, A PROCESS FOR THE PRODUCTION AND USE

The invention concerns a new recombinant D-hydantoinase, a process for its production and its use.

D-hydantoinases (dihydropyrimidinases, EC 3.5.2.2) are used to produce N-carbamoyl-D-amino acids. These compounds are important intermediate products for the production of D-amino acids (Morin et al., Appl. Microbiol. 35, 536–540 (1991), EP-B 0 219 034). D-amino acids are, in turn important starting materials for the synthesis of the side chains of penicillins and semi-synthetic cephalosporins. The production of N-carbamoyl-D-amino acids is preferably carried out at higher temperatures since the hydantoins are then more soluble, the racemisation takes place more rapidly and the reaction is also accelerated. For this reason there is a need for thermostable D-hydantoinases.

A D-hydantoinase which is active at high temperatures (40°–90° C.) can be obtained from thermophilic microorganisms (DE-A 30 31 151). However, these thermophilic microorganisms are difficult to cultivate and grow poorly. In addition D-hydantoinase is only produced in very small amounts by these microorganisms.

A recombinant D-hydantoinase is described in EP-B 0 219 034. However, D-hydantoinase activity is only obtained in a small amount during expression of the DNA sequences described in EP-B 0 219 034.

BRIEF SUMMARY OF THE INVENTION

The object of the present invention was to provide a recombinant D-hydantoinase with a further improved temperature stability in large amounts.

This object is achieved by a protein which has D-hydantoinase activity and is characterized by the amino acid sequence SEQ ID NO 1.

DETAILED DESCRIPTION

Figure 1:
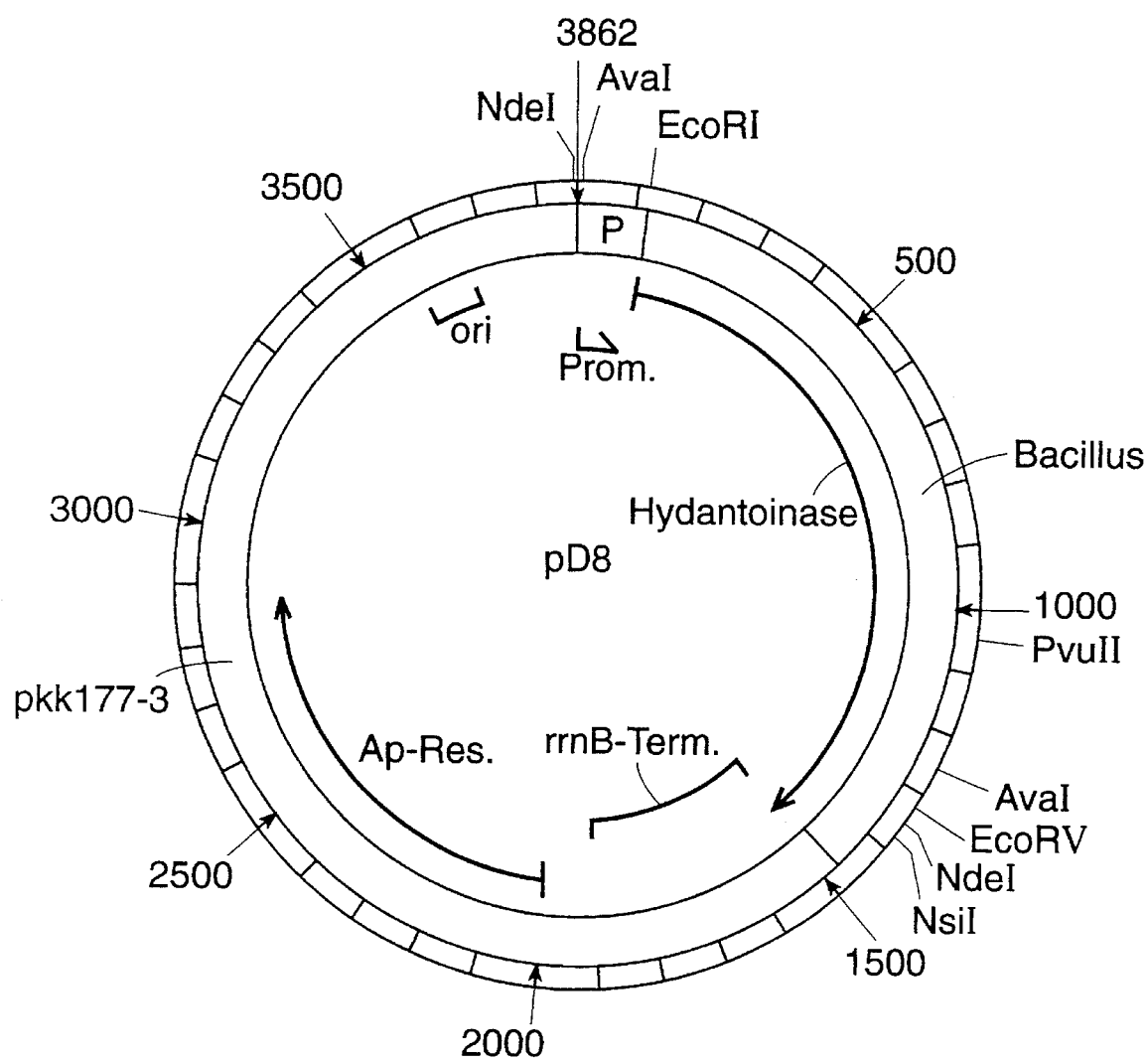
FIG. 1 presents a restriction endonuclease map of a plasmid used to express the D-hydantoinase of the invention.

The protein has
a) optional activity at a pH of about 8.2, and is optimally stable at a pH range of from about 6.5 to about 9.0,
b) has about 100% of its initial activity in 50 mmol/l Tris buffer, pH 7.8 at a concentration of 15 mg/ml after 20 minutes at 60° C. and still ca. 80% of the initial activity after 20 minutes at 65° C.,
c) is a polypeptide that does not occur naturally,
d) is the product of a prokaryotic expression of an exogenous DNA.

It surprisingly turned out that the enzyme according to the invention can be produced recombinantly in prokaryotes in large amounts, is readily soluble has high activity and good temperature stability.

The recombinant D-hydantoinase according to the invention differs from the native enzyme (wild-type enzyme) obtained from thermophilic bacillus (DE-OS 30 31 151) and from the enzyme described in EP-B 0 219 034 with regard to the amino acid sequence at the C-terminus.

The enzyme according to the invention is 12 amino acids shorter than the wild-type enzyme and differs in the sequence of the last 6 amino acids. In other words, the enzyme of the invention is 460 amino acids long, as compared to wild type, which is 472 amino acids long. Further, when the enzyme of the invention is compared to wild type, they differ at amino acids 455–460. Compared to the enzyme described in EP-B 0 219 034, the enzyme according to the invention is 8 amino acids longer and differs in the sequence of the last 30 amino acids. In other words, the enzyme in EP 0 219 034 is 452 amino acids long. Its last 22 amino acids differ as compared to the positions in the enzyme of the invention.

D-hydantoinases according to the invention are also understood as those proteins whose amino acid sequence differs slightly from SEQ ID NO 1. In this case amino acids can be substituted, deleted, derivatized or added.

A nucleic acid molecule, e.g., DNA, is used for the recombinant production of D-hydantoinase according to the invention. It codes for a protein with D-hydantoinase activity and is selected from the group consisting of
a) the DNA sequence shown in sequence ID NO 2 or the complementary DNA sequence thereto,
b) DNA sequences which due to the degeneracy of the genetic code, code for a protein which is also coded by one of the sequences defined in a).

A DNA sequence of sequence ID NO 2 is preferably used.

The DNA sequences can be slightly modified in a manner familiar to a person skilled in the art. For example degenerate codons can be replaced by other codons which code for the same amino acid. Furthermore additional codons can be inserted at the 5' and the 3' end or also within the sequences or individual codons or groups of codons can be deleted provided that the DNA variants obtained in this manner only differ slightly from the sequences according to the invention, hybridize with these sequences under the usual conditions (Sambrook et al., Molecular Cloning, A Laboratory Manual, Cold Spring Harbor Laboratory Press, New York 1989) and the coded protein has D-hydantoinase activity.

The invention also concerns a process for the production of recombinant D-hydantoinase by transformation of a suitable prokaryotic eukaryotic host cell (e.g. *E. coli*, *Saccharomyces cervisiae*) with DNA according to the invention which is present in a suitable expression system, culture of the transformed host cells and isolation of the D-hydantoinase formed from the cells or the cell supernatant.

The transformation of the host cells used for the recombinant production is carried out according to known methods (Sambrook et al. supra 1989). The transformed host cells are cultured under conditions which allow expression of the D-hydantoinase gene. Depending on the expression vector used, it may be necessary to add an inducer (e.g. lactose or isopropyl-β-D-thiogalactopyranoside (IPTG)) in a known manner to the culture medium. The isolation of the recombinant D-hydantoinase from the cell supernatant or the cells is carried out in a known manner.

Using this process it is possible to obtain recombinant, active D-hydantoinase in a yield of up to $10^6$ U/1.5 kg biomass.

Lysis and purification of the recombinantly produced D-hydantoinase can be carried out according to methods familiar to a person skilled in the art. The biomass obtained after fermentation is preferably disrupted in a high pressure homogenizer, the crude extract fractionated with ammonium sulfate and incubation at ca. 60° C. (heat step).

The invention in addition concerns a process for cleaving a racemic hydantoin into the corresponding N-carbamoyl-D-amino acid which is characterized in that the racemic hydantoin is incubated with a D-hydantoinase according to the invention at a temperature of 50°–80° C. and the N-carbamoyl-D-amino acid that is formed is subsequently isolated and if desired purified from the reaction mixture according to methods familiar to a person skilled in the art.

All genetic engineering methods such as e.g. expression, DNA modification, cloning and isolation of the recombinant protein can be carried out according to methods familiar to a person skilled in the art such as those described in Ausubel, F. M., et al., Current Protocols in Molecular Biology, Wiley, New York 1992; Sambrook et al., supra, or Davis, L. G., Methods in Molecular Biology, Elsevier, Amsterdam, NL, 1986.

The invention is elucidated in more detail by the following examples, the sequence protocol and the figure:

EXAMPLE 1

Plasmid Construction

A D-hydantoinase gene is isolated from Bacillus thermoglucosidasius (wild type) using two primers (Hyd1 and Hyd2) and inserted after restriction with the restriction enzymes EcoRI and HindIII into a suitable expression vector for expression in E. coli (pKK177-3, DSM 3062).

Hyd1: GGAATTCTATGACAAAAATAATAAAAAATGG (SEQ ID NO 3)

Hyd2: GCGGATCCAAGCTTTTAAATATTGGCCGTACCC (SEQ ID NO 4)

If a base is deleted from the HindIII cleavage site (AAGCTT→AAGCT) then a reading frame is formed that can be translated into a protein having SEQ ID NO 1 (FIG. 1).

The resulting plasmid pD8 contains SEQ ID NO 2 as the protein-coding sequence under the control of an IPTG-inducible promoter. In this plasmid the promoter can be replaced by other promoters such as e.g. by the lac promoter, mgl promoter (EP-A 0 316 370) or by the promoters described in EP-A 0 186 069 and EP-A 0 303 925.

EXAMPLE 2

Description of the Fermentation Process for Recombinant Hydantoinase from E. coli E. coli HB 101 (DSM 1607) is used as the host organism which contains pD8 as well as the lacI gene on a compatible plasmid.

The precultures were cultured in LB medium with double selection pressure (kanamycin and ampicillin) starting from paillettes stored in liquid nitrogen.

The inoculation volume for the main culture is 1–10% by volume. The main components of the HK medium are yeast extract and glucose. The medium is adjusted with $K_2HPO_4$ to pH 7.6–7.8 before the inoculation.

Further essential components of the medium are Mn and Mg salts. They are necessary for the activity and stability of the hydantoinase. The salts are sterilized separately and added separately to the medium. Only a small amount (ca. 20%) is added first, the main amount is added via a glucose dosage which is used as a regulator of acidity.

In order to avoid formation of inclusion bodies (IBs), induction with a small amount of IPTG (<1 mmol) is not carried out until an $OD_{578}$ of 10 is achieved. The fermentation temperature is 32° C. In addition, above $OD_{578}$=30 a limiting dose of yeast extract is added to limit the growth rate.

By regulating and limiting the specific growth rate via the dosage rate, it is possible to almost completely suppress IB formation and achieve a high yield of biomass. The pH value is regulated at 7.0–7.2. In order to suppress undesired acid formation the dissolved oxygen value $pO_2$ is kept at >10% by means of the stirrer speed, inlet air control, dosage rate and/or pressure.

An $OD_{578}$ of 120–140 is achieved after a fermentation period of about 40 hours. This represents a biomass yield of 45–50 g dry weight/l. The hydantoinase activity is in this case >1 MU/l which corresponds to an expression rate of >10 g/l of active, soluble hydantoinase at a specific activity of about 100 U/mg.

EXAMPLE 3

3.1 Disruption 1.5 kg wet biomass is suspended in 6 liters cold 50 mmol/l TRIS/HCl buffer pH 8.5 and disrupted with a high pressure homogenizer from the APV Gaulin GmbH Company at 1200 bar. The suspension is subsequently cooled to +4° C. and centrifuged at high speed at ca. 25,000×g in a Sorvall centrifuge.

3.2 Ammonium sulfate fractionation

Solid ammonium sulfate is added to the crude extract up to a concentration of 1.3 mol/l, the precipitate is discarded by centrifugation at high speed. The supernatant is precipitated further with ammonium sulfate up to a concentration of 2.5 mol/l and the precipitate is again centrifuged at high speed.

3.3 Heat step

The precipitate of the ammonium sulfate precipitation is dissolved with 50 mmol/l TRIS/HCl buffer pH 8.5 and adjusted to a protein concentration of 10 mg/ml. The enzyme solution is heated to 56° C. and kept at this temperature for 30 minutes; subsequently it is cooled to +4° C. and the precipitate is centrifuged.

The yield is about $1\times10^6$ units with a specific activity of 35 U/mg protein.

3.4 Comparison with the state of the art

Table 1 shows a comparison of the activities expressed per liter for the known hydantoinases and for the enzyme according to the invention.

TABLE 1

| D-hydantoinase | Activity in kU/l |
| --- | --- |
| according to DE-A 30 31 151 (wild type) | 0.10 |
| according to EP-B 0 219 034 | 0.56 |
| according to the invention | 1000 |

We claim:

1. Isolated protein having D-hydantoinase activity consisting of the amino acid sequence set forth in SEQ ID NO: 1, wherein said isolated protein retains about 100% of said D-hydantoinase activity after 20 minutes at 60° C., when present in a 50 m mol/l Tris buffer, pH 7.8, at a concentration of 15 mg/ml, and retains about 80% of said D-hydantoinase activity after 20 minutes at 65° C., in a 50 m mol/l Tris buffer, at pH 7.8.

* * * * *

SEQUENCE LISTING ( 1 ) GENERAL INFORMATION:

( i i i ) NUMBER OF SEQUENCES: 4

( 2 ) INFORMATION FOR SEQ ID NO: 1:

( i ) SEQUENCE CHARACTERISTICS:

( A ) LENGTH: 460 amino acids
( B ) TYPE: amino acid
( C ) STRANDEDNESS: single
( D ) TOPOLOGY: linear ( x i ) SEQUENCE DESCRIPTION: SEQ ID NO: 1:

```
Met Thr Lys Ile Ile Lys Asn Gly Thr Ile Val Thr Ala Thr Asp Thr
 1               5                  10                  15

Tyr Glu Ala Asp Leu Leu Ile Lys Asp Gly Lys Ile Ala Met Ile Gly
             20                  25                  30

Gln His Leu Glu Glu Lys Gly Ala Glu Val Ile Asp Ala Lys Gly Cys
             35                  40                  45

Tyr Val Phe Pro Gly Gly Ile Asp Ser His Thr His Leu Asp Met Pro
         50                  55                  60

Phe Gly Gly Thr Val Thr Lys Asp Asp Phe Glu Ser Gly Thr Ile Ala
 65                  70                  75                  80

Ala Ala Phe Gly Gly Thr Thr Thr Ile Ile Asp Phe Cys Leu Thr Asn
                 85                  90                  95

Lys Gly Glu Pro Leu Lys Lys Ala Ile Glu Thr Trp His Asn Lys Ala
            100                 105                 110

Lys Gly Lys Ala Val Ile Asp Tyr Gly Phe His Leu Met Ile Ser Glu
            115                 120                 125

Ile Thr Asp Asp Val Leu Glu Glu Leu Pro Lys Val Ile Ala Glu Glu
    130                 135                 140

Gly Ile Thr Ser Phe Lys Val Phe Met Ala Tyr Lys Asn Val Phe Gln
145                 150                 155                 160

Ala Asp Asp Gly Thr Leu Tyr Arg Thr Leu Val Ala Ala Lys Glu Leu
                165                 170                 175

Gly Ala Leu Val Met Val His Ala Glu Asn Gly Asp Val Ile Asp Tyr
            180                 185                 190

Leu Thr Lys Lys Ala Leu Ala Glu Gly Asn Thr Glu Pro Ile Tyr His
    195                 200                 205

Ala Leu Thr Arg Pro Pro Glu Val Glu Gly Glu Ala Thr Gly Arg Ala
210                 215                 220

Cys Gln Leu Thr Glu Leu Ala Gly Ser Gln Leu Tyr Val Val His Val
225                 230                 235                 240

Thr Cys Ala Gln Ala Val Glu Lys Ile Ala Gln Ala Arg Asn Lys Gly
                245                 250                 255

Leu Asp Val Trp Gly Glu Thr Cys Pro Gln Tyr Leu Val Leu Asp Gln
            260                 265                 270

Ser Tyr Leu Glu Lys Pro Asp Phe Glu Gly Ala Lys Tyr Val Trp Ser
    275                 280                 285

Pro Pro Leu Arg Glu Lys Trp His Gln Glu Val Leu Trp Asn Ala Leu
290                 295                 300

Lys Asn Gly Gln Leu Gln Thr Leu Gly Ser Asp Gln Cys Ser Phe Asp
305                 310                 315                 320

Phe Lys Gly Gln Lys Glu Leu Gly Arg Gly Asp Phe Thr Lys Ile Pro
                325                 330                 335

Asn Gly Gly Pro Met Val Glu Asp Arg Val Ser Ile Leu Phe Ser Glu
            340                 345                 350

Gly Val Lys Lys Gly Arg Ile Thr Leu Asn Gln Phe Val Asp Ile Met
    355                 360                 365

Ser Thr Arg Ile Ala Lys Leu Phe Gly Leu Phe Pro Arg Lys Gly Thr
370                 375                 380
```

| Ile | Ala | Val | Gly | Ser | Asp | Ala | Asp | Leu | Val | Ile | Phe | Asp | Pro | Asp | Ile |
| --- | --- | --- | --- | --- | --- | --- | --- | --- | --- | --- | --- | --- | --- | --- | --- |
| 385 | | | | | 390 | | | | | 395 | | | | | 400 |

| Glu | Arg | Val | Ile | Ser | Ala | Glu | Thr | His | His | Met | Ala | Val | Asp | Tyr | Asn |
| --- | --- | --- | --- | --- | --- | --- | --- | --- | --- | --- | --- | --- | --- | --- | --- |
| | | | | 405 | | | | | 410 | | | | | 415 | |

| Ala | Phe | Glu | Gly | Met | Lys | Val | Thr | Gly | Glu | Pro | Val | Ser | Val | Leu | Cys |
| --- | --- | --- | --- | --- | --- | --- | --- | --- | --- | --- | --- | --- | --- | --- | --- |
| | | | 420 | | | | | 425 | | | | | 430 | | |

| Arg | Gly | Glu | Phe | Val | Val | Arg | Asp | Lys | Gln | Phe | Val | Gly | Lys | Pro | Gly |
| --- | --- | --- | --- | --- | --- | --- | --- | --- | --- | --- | --- | --- | --- | --- | --- |
| | | 435 | | | | | 440 | | | | | 445 | | | |

| Tyr | Gly | Gln | Tyr | Leu | Lys | Ala | Gly | Cys | Phe | Gly | Gly |
| --- | --- | --- | --- | --- | --- | --- | --- | --- | --- | --- | --- |
| | 450 | | | | | 455 | | | | 460 | |

(2) INFORMATION FOR SEQ ID NO: 2:

(i) SEQUENCE CHARACTERISTICS:
        (A) LENGTH: 1383 base pairs
        (B) TYPE: nucleic acid
        (C) STRANDEDNESS: single
        (D) TOPOLOGY: linear (xi) SEQUENCE DESCRIPTION: SEQ ID NO: 2:

```
ATGACAAAAA TAATAAAAAA TGGAACGATT GTTACCGCAA CCGATACGTA TGAAGCGGAC    60
TTGCTCATTA AAGACGGAAA AATTGCCATG ATAGGCCAAC ATTTAGAAGA AAAAGGCGCT   120
GAAGTGATTG ATGCCAAAGG CTGTTACGTA TTTCCAGGCG GTATTGATTC GCACACGCAT   180
TTAGATATGC CGTTTGGCGG CACGGTGACA AAGGATGATT TCGAATCTGG AACGATTGCG   240
GCGGCATTTG GCGGAACAAC GACCATCATC GACTTTTGTT AACGAATAA AGGGGAGCCA    300
TTAAAAAAAG CGATTGAAAC TTGGCACAAC AAAGCGAAGG GAAAAGCGGT TATTGATTAT   360
GGCTTCCATT TAATGATTAG CGAAATTACG GATGACGTAT TAGAAGAGCT GCCAAAAGTC   420
ATTGCCGAAG AAGGGATAAC ATCCTTTAAA GTGTTTATGG CGTATAAAAA CGTATTTCAG   480
GCAGATGATG GAACGTTATA CCGCACGCTA GTGGCTGCCA AGAACTTGG CGCGCTTGTC    540
ATGGTTCATG CGGAAAATGG GGATGTGATT GATTACTTAA CGAAAAAAGC GCTTGCGGAA   600
GGGAATACGG AGCCGATTTA CCATGCTTTA ACGCGGCCTC AGAAGTAGA AGGAGAAGCG    660
ACCGGGCGCG CCTGTCAATT GACAGAGCTT GCCGGTTCAC AACTTTACGT TGTTCACGTG   720
ACATGTGCGC AAGCGGTGGA AAAAATTGCA CAAGCGCGCA ATAAAGGGTT GGATGTGTGG   780
GGAGAAACGT GTCCGCAATA TCTTGTTCTC GACCAATCGT ATTTAGAAAA GCCTGATTTT   840
GAAGGCGCGA AATATGTTTG GTCCCCTCCG CTTCGTGAAA AATGGCATCA AGAAGTATTG   900
TGGAATGCGC TGAAAAACGG CCAGCTGCAA ACGCTTGGAT CGGACCAATG TTCATTTGAC   960
TTTAAAGGCC AAAAAGAACT TGGCAGAGGA GATTTTACTA AAATTCCAAA CGGCGGGCCG  1020
ATGGTCGAGG ATCGGGTCAG CATTCTTTTC AGTGAAGGGG TTAAAAAAGG AAGAATCACG  1080
TTAAATCAAT TTGTCGATAT TATGTCGACA AGAATTGCCA AATTGTTCGG GTTATTCCCG  1140
AGAAAAGGAA CGATCGCGGT AGGTTCAGAC GCAGACTTAG TCATTTTTGA CCCGGATATC  1200
GAACGGGTGA TTTCGGCGGA AACACACCAT ATGGCCGTCG ACTATAATGC ATTTGAAGGA  1260
ATGAAAGTAA CGGGTGAACC GGTATCGGTT CTGTGCAGAG GCGAATTTGT TGTCCGTGAT  1320
AAACAATTTG TCGGAAAACC AGGGTACGGC CAATATTTAA AAGCTGGCTG TTTTGGCGGA  1380
TGA                                                                1383
```

(2) INFORMATION FOR SEQ ID NO: 3:

(i) SEQUENCE CHARACTERISTICS:
        (A) LENGTH: 31 base pairs
        (B) TYPE: nucleic acid (C) STRANDEDNESS: single
(D) TOPOLOGY: linear (xi) SEQUENCE DESCRIPTION: SEQ ID NO: 3:

GGAATTCTAT GACAAAAATA ATAAAAAATG G 31

(2) INFORMATION FOR SEQ ID NO: 4:

(i) SEQUENCE CHARACTERISTICS:
(A) LENGTH: 33 base pairs
(B) TYPE: nucleic acid
(C) STRANDEDNESS: single
(D) TOPOLOGY: linear (xi) SEQUENCE DESCRIPTION: SEQ ID NO: 4:

GCGGATCCAA GCTTTTAAAT ATTGGCCGTA CCC 33